United States Patent
Schechter et al.

(10) Patent No.: US 7,832,394 B2
(45) Date of Patent: Nov. 16, 2010

(54) APPARATUS FOR DISPENSING PRESSURIZED CONTENTS

(76) Inventors: Alan M. Schechter, 3301 Marna Ave., Long Beach, CA (US) 90808-3251;
Adam M. Schechter, 3301 Marna Ave., Long Beach, CA (US) 90808-3251

( * ) Notice: Subject to any disclaimer, the term of this patent is extended or adjusted under 35 U.S.C. 154(b) by 1650 days.

(21) Appl. No.: 11/021,743

(22) Filed: Dec. 22, 2004

(65) Prior Publication Data
US 2006/0130832 A1    Jun. 22, 2006

(51) Int. Cl.
*A61M 15/00*    (2006.01)
*A61M 11/00*    (2006.01)
*A61M 16/00*    (2006.01)

(52) U.S. Cl. .............. 128/200.24; 128/200.11; 128/200.14; 128/200.19; 128/200.23; 128/203.12; 128/203.13; 128/203.14; 128/203.15; 128/203.25; 128/203.26; 128/203.27

(58) Field of Classification Search ............ 128/200.11, 128/200.14, 200.19, 200.23, 203.12, 203.13, 128/203.14, 203.15, 203.25, 203.26, 203.27
See application file for complete search history.

(56) References Cited

U.S. PATENT DOCUMENTS

| | | | |
|---|---|---|---|
| 4,648,393 A | 3/1987 | Landis et al. | |
| 4,803,978 A | 2/1989 | Johnson, IV et al. | |
| 4,896,832 A | 1/1990 | Howlett | |
| 5,347,998 A | 9/1994 | Hodson et al. | |
| 5,363,842 A | 11/1994 | Mishelevich et al. | |
| 5,505,195 A | 4/1996 | Wolf et al. | |
| 5,544,647 A | 8/1996 | Jewett et al. | |
| 5,622,163 A | 4/1997 | Jewett et al. | |
| 5,676,129 A | 10/1997 | Rocci, Jr. et al. | |
| 5,743,251 A | 4/1998 | Howell et al. | |
| 5,743,252 A | 4/1998 | Rubsamen et al. | |
| 5,755,218 A | 5/1998 | Johansson et al. | |
| 5,809,997 A | 9/1998 | Wolf | |
| 6,012,450 A | 1/2000 | Rubsamen | |
| 6,138,669 A | 10/2000 | Rocci, Jr. et al. | |
| 6,202,642 B1 | 3/2001 | McKinnon et al. | |
| 6,260,549 B1 | 7/2001 | Sosiak | |
| 6,557,552 B1 | 5/2003 | Cox et al. | |
| 6,651,651 B1 | 11/2003 | Bonney et al. | |
| 6,752,145 B1 | 6/2004 | Bonney et al. | |
| 6,886,557 B2 * | 5/2005 | Childers et al. | 128/200.14 |
| 6,932,083 B2 | 8/2005 | Jones et al. | |
| 7,066,913 B2 * | 6/2006 | Kullik et al. | 604/246 |

(Continued)

*Primary Examiner*—Patricia M Bianco
*Assistant Examiner*—Nihir Patel
(74) *Attorney, Agent, or Firm*—BioTechnology Law Group; Daniel M. Chambers

(57) ABSTRACT

Containers for incrementally dispensing pressurized contents are described. The containers comprise a vessel suited to contain pressurized contents, a port integral with the vessel and through which pressurized contents contained in the vessel can be released from the vessel, preferably incrementally in approximately equal amounts, and a measuring device disposed in the vessel. The measuring device senses ambient conditions in the vessel and, directly or with other components, indicates, for example, the amount of pressurized contents remaining in the vessel and displaying it to an observer; methods for comparing the amount of contents actually released from the vessel compared to a theoretical constant; and methods for time logging (alone or in conjunction with the logging of other data) the actuation of the dispensing valve for comparison to a prescribed method. Devices (including metered dose inhalers) for incrementally dispensing pressurized contents from such containers are also described.

35 Claims, 7 Drawing Sheets

1. Actuator
2. Canister (Container and Metering Valve)
3. Transfer Channel
4. Core Extension
5. Adapter
6. Medicine Exit Hole of Core Extension
7. Medication Exit Port
8. Micro switch – sensing mechanical actuations
9. Pressure Sensor in Transfer Channel
10. Sensor Inside Canister

U.S. PATENT DOCUMENTS

| | | |
|---|---|---|
| 2002/0069876 A1 | 6/2002 | Loser et al. |
| 2002/0168322 A1 | 11/2002 | Clark et al. |
| 2003/0010337 A1 | 1/2003 | Anderson et al. |
| 2003/0101991 A1 | 6/2003 | Trueba |
| 2003/0106550 A1 | 6/2003 | Harvey |
| 2003/0183226 A1 | 10/2003 | Brand et al. |
| 2003/0192534 A1 | 10/2003 | Klump et al. |

* cited by examiner

1. Actuator
2. Canister (Container and Metering Valve)
3. Transfer Channel
4. Core Extension
5. Adapter
6. Medicine Exit Hole of Core Extension
7. Medication Exit Port
8. Micro switch – sensing mechanical actuations
9. Pressure Sensor in Transfer Channel
10. Sensor Inside Canister Figure 4
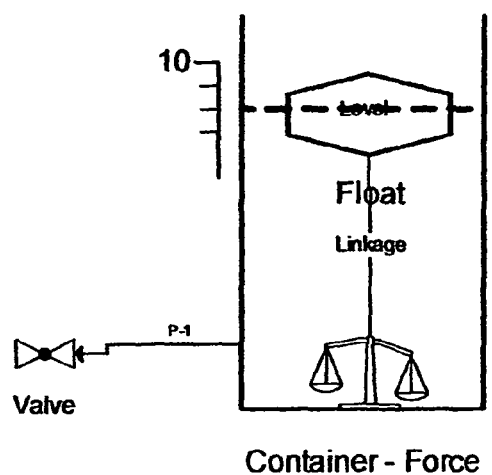
Container - Force
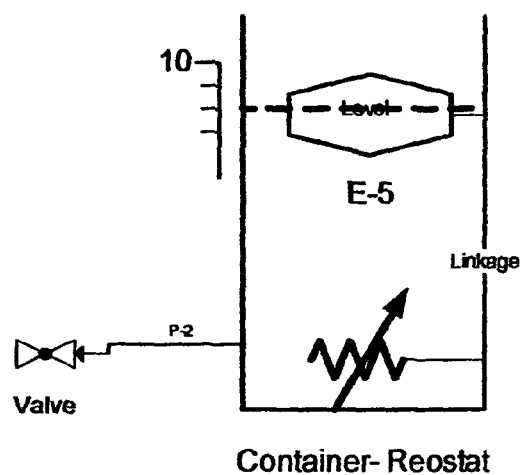
Container - Reostat

APPARATUS FOR DISPENSING PRESSURIZED CONTENTS

TECHNICAL FIELD

The present invention relates generally to containers for incrementally dispensing pressurized contents; more specifically, to containers comprising a measuring device capable of sensing an amount of pressurized contents within the container and arranged to output a signal representative of the amount of the pressurized contents within the container.

BACKGROUND OF THE INVENTION

1. Introduction

The following description includes information that may be useful in understanding the present invention. It is not an admission that any such information is prior art, or relevant, to the presently claimed inventions, or that any publication specifically or implicitly referenced is prior art.

2. Background

For the past several decades, scientists and engineers have researched and developed techniques for the delivery of pressurized contents, such as aerosols, for a wide range of applications. Today, such techniques are a part of everyday life as there are thousands of products packaged in aerosol cans—everything from air fresheners to insect repellants to paint to deodorant to hair spray to cooking oil to medicines. The most common techniques for generating aerosols involve the use of a compressed propellant such as methylchloroform or chlorofluoro-carbon (CFC) to entrain the material. Aerosol cans (typically made of metal) come in many shapes and sizes but all work on the same basic principle: one high-pressure fluid (or gas) forces another fluid (or particles) through a nozzle. An aerosol can contains one fluid that boils well below room temperature (called the propellant) and one that boils at a much higher temperature (called the product). The product is the substance actually intended to be delivered—the hair spray, insect repellent paint, or medicine, for example—and the propellant is used to get the product out of the can.

There are two ways to configure this aerosol system. In the simpler configuration (compressed-gas system), liquid product is poured into the can, the can is sealed, and then a gaseous propellant is pumped into the can at high pressure through a valve system. A typical configuration of a compressed gas aerosol can is as follows: a long plastic tube runs from the bottom of the can up to a valve system at the top of the can. The valve has a small, depressible headpiece, with a narrow channel running through it. The channel runs from an inlet near the bottom of the headpiece to a small nozzle at the top. A spring pushes the head piece up, so the channel inlet is blocked by a tight seal. When the headpiece is depressed, the inlet slides below the seal, opening a passage from the inside of the can to the outside. The high-pressure propellant gas drives the liquid product up the plastic tube and out through the nozzle. The narrow nozzle serves to atomize the flowing liquid, break it up into tiny droplets that form a fine spray.

In the second and more popular aerosol system (liquefied-gas system), the propellant is a liquefied gas. This means that the propellant will take liquid form when it is highly compressed, even if it is kept well above its boiling point. Since the product is liquid at room temperature, it is simply poured in before the can is sealed. The propellant, on the other hand, must be pumped in under high pressure after the can is sealed. When the propellant is kept under high enough pressure, it cannot expand into a gas. It thus stays in liquid form as long as the pressure is maintained. The actual aerosol can design in the liquefied-gas system may be the same as in the compressed-gas system, but functions differently when the headpiece is depressed. In the liquefied-gas system, when the valve is opened, the pressure on the liquid propellant is instantly reduced. With less pressure, it can begin to boil. Particles break free, forming a gas layer at the top of the can. This pressurized gas layer pushes the liquid product, as well as some of the liquid propellant, up the tube to the nozzle. Some cans, such as spray-paint cans, have a ball-bearing inside. If you shake the can, the rattling ball bearing helps to mix up the propellant and the product, so the product is pushed out in a fine mist. When the liquid flows through the nozzle, the propellant rapidly expands into gas. In some aerosol cans, this action helps to atomize the product, forming an extremely fine spray. In other designs, the evaporating propellant forms bubbles in the product, creating foam. The consistency of the expelled product depends on several factors, including: the chemical makeup of the propellant and product; the ratio of propellant to product; the pressure of the propellant; and the size and shape of the valve system. Manufacturers produce a wide variety of aerosol devices by configuring these elements in different combinations. While widely used, such aerosol devices remain somewhat limited because: the particles dispersed are too large for certain applications; currently there is no effective way of monitoring the amount of contents remaining in the can at any given time; and the most popular conventional propellants have adverse environmental effects.

Techniques for the delivery of pressurized contents in the form of an aerosol comprising therapeutic compositions, e.g., aerosol sprays of fine particles of liquid and/or solid compositions that contain therapeutic agents, are well known and have seen many improvements. For example, conventional devices for delivering aerosol medication for inhalation by a patient include metered dose inhalers (MDI). Such devices are designed to afford proper coordination of the delivery of a dose of therapeutic agent with inhalation by a patient to allow the proper dose of the therapeutic agent to be drawn into the patient's bronchial passages. There are currently also propellant-free dry powered inhalers on the market but such devices have known disadvantages, including an inability to deliver more than about 10% of the inhaled therapeutic agent to the distal regions of the lung (e.g., the alveoli) where it can be absorbed into the blood stream, patients being unable to inhale rapidly enough to use such devices properly, and loss of the therapeutic agent if the patient exhales through the device.

MDIs are the most commonly used and prescribed medication delivery systems used to deliver inhaled medications for treatment of a variety of conditions, including bronchodilator therapy. MDIs may be manually operated or breath-activated devices. Breath-activated MDIs provide a metered dose automatically when the patient's respiratory effort actuates the device. See, for example, U.S. Pat. Nos. 6,260,549; 4,648,393; 4,803,978; and 4,896,832. The key problems associated with breath-activated devices include: the patient's inspiration effort may not be sufficient to trigger the release of the metered dose either all of the time or some of the time; and, the patient's inspiration effort may be sufficient to trigger release of the metered dose, but not sufficient to cause the medication to pass into the desired portion of the patient's airways. Such problems cause patient frustration, inconsistent or inadequate medicament delivery, and may lead to ineffective therapy.

While conventional MDIs provide tremendous benefit for bronchodilator, steroid, and other drug delivery, there are still several limitations and problems associated with MDIs that need to be addressed in order to improve patient compliance and overall patient care. For example, because proper use of manually operated MDIs requires the patient to perform several important steps, patient error often adversely effects delivery of the aerosol to the desired site and the patient does not receive the appropriate dose. Such errors include: lack of coordination between actuation of the device and inspiration; inadequate inspiratory flow; inadequate breath holding; and inadequate deep inhalation. In addition, patients are often required to agitate the contents of the container for 2-4 seconds to fully mix the components, and are cautioned to use the MDI only within a certain temperature range (e.g., 15-30 degrees C.). While these problems can be addressed through patient education and training, such training is often still inadequate.

MDI design can also lead to problems of ineffective delivery and improper doses being administered. For young children and elderly patients, insufficient hand strength may result in inadequate manual pressure to actuate a device that requires a patient to simultaneously apply manual pressure to both the top and bottom of the device to activate it, or may result in a partial actuation, thereby delivering an insufficient dose. When the patient fails to receive the prescribed dose, his/her may not obtain the expected benefit and will then overuse the medication, thereby increasing the risk of adverse side effects. Conversely, failure to obtain the expected benefit may lead to the patient to stop taking the medication altogether. There thus exists a need for a device that is easy to actuate and which provides a way for the patient to monitor their correct usage of the device, so as to improve patient compliance and treatment.

In addition, patients often run out of medication because they are unable to monitor or estimate the amount of medication remaining in the device at any given time. MDI manufacturers typically label the MDI or the MDI product insert with a maximum number of doses to be delivered, and the patient is cautioned that the MDI should be discarded when the prescribed number of doses has been dispensed, "even though the canister is not completely empty" (see, e.g., the package insert for Albuterol). Patients using MDI products are therefore forced to manually log the doses administered for each MDI and subtract the doses administered from the total guaranteed maximum number of doses in the new container in order to compute the remaining in the container. This method of computing the number of doses remaining in the container is inconvenient, and prone to patient-induced book keeping errors. Most importantly, this method of computing is inaccurate because the patient is, in effect, counting the number of MDI metering valve actuations while assuming that the prescribed dose of therapeutic agent is being dispersed and evacuated from the container upon each actuation. In fact, if some of the actuations occurred when the ambient temperature was outside of the recommended parameters for the MDI, the dose administered would be either higher or lower than expected and the number of doses remaining in the container would be proportionally inaccurate. Specifically, high ambient temperature conditions lead to dispensing more therapeutic agent and low ambient temperature conditions cause less to be dispensed. Finally, foreign material obstructions in or near the metering valve or transfer channel may also reduce the amount of therapeutic agent received compared to that which was expected. In effect, the patient has no real knowledge of the number of doses remaining in the container and may leave home with an MDI that does not contain an adequate supply of therapeutic agent, which can have life-threatening consequences.

Several approaches to solving these problems have been described in the literature. For example, some health advocate organizations recommend directly measuring the amount of medication in the container by removing the container from the actuator and then immersing the container in a container of water. An observation of full immersion purportedly indicates a full container; a partially surfaced but vertical orientation indicates that the container is about half full; an inclined, floating container indicates that the container is about one-fourth full; and a horizontal floating container indicates that the container is empty (see Palo Alto Medical Foundation, a Sutter Health Affiliate). Also, it is presumed that some patients may develop a qualitative feel for the amount of medication remaining in the container, as they must shake or agitate the contents before use. These methods are clearly unreliable, inaccurate, and may be dangerous.

In response to these problems, several approaches have been taken. For example, devices have been developed for dispensing therapeutic agents that use an inductive displacement transducer to monitor airflow across the dispensing part of the device to create an actuation profile which can be used by the patient to monitor correct usage of the device. In such devices, the transducer measures the relative proximity of the device container to the device housing. In another approach, the apparatus directly counts the number of doses expended from a MDI by using a pressure sensor and/or an electronic sensor and a microprocessor to detect pressure pulse/airflow in the transfer channel of the mouthpiece of the MDI. The microprocessor processes data reflective of the pressure pulse/airflow and displays the doses remaining. Still another approach involves a medication dispenser that uses an actuation-indicator, employed as an add-on to an inhalation device, for detecting movement of the inhalation device container relative to the inhalation device housing. Breath-activated inhalers that employ a microprocessor to control activation and medication release based on flow rate and time interval from start of inspiration have also been developed. Such a device reportedly allows for optimal delivery of medication upon each activation. Another type of therapeutic agent dispenser utilizes two transceivers to provide for a two-way transfer of data to allow the patient to monitor dose counts and correct usage.

While such approaches have advanced the technology, there clearly still exists a need for a device that provide the capability to allow a patient to more accurately determine the quantity of pressurized contents in the container at any given time.

All the foregoing patents measure conditions in the transfer channel and derive does remaining in the container. We directly measure the contents of the container.

SUMMARY OF THE INVENTION

It is an object of the present invention to provide a measuring device for containers that incrementally dispense pressurized contents. In one aspect, the container comprises a vessel suited to contain pressurized contents, a port integral with the vessel and through which pressurized contents contained in the vessel can be released from the vessel, and a measuring device disposed in the vessel. If necessary, one or more separate ports can also be provided for filling the container with contents (e.g., products and propellants). The measuring device is capable of sensing an amount of the pressurized contents within the vessel, and it is arranged to output a signal representative of the amount of the pressurized contents within the vessel. Importantly, the ability to monitor the amount of pressurized contents within the vessel allows the user to determine the amount of pressurized contents remaining in the container upon each actuation. Moreover, the user (e.g., a patient) can assess whether an intended quantity (e.g., dosage of medicine) has been delivered from the device following a given actuation.

It is a further object of the present invention to provide an apparatus for incrementally dispensing pressurized contents from a container. In some embodiments, the apparatus comprises a container comprising a vessel suited to contain pressurized contents, a port integral with the vessel and through which pressurized contents contained in the vessel can be released from the vessel, a measuring device disposed in the vessel, and a dispenser functionally coupled to the port of the container that provides for incrementally dispensing at least a portion of the pressurized contents in the vessel upon actuation of the dispenser. In preferred embodiments, the dispenser forms a portion of a housing that supports the container, and the housing is arranged to serve as an actuator for the dispenser. Again, the measuring device is capable of sensing an amount of the pressurized contents within the vessel, and it is arranged to output a signal representative of the amount of the pressurized contents within the vessel In certain preferred embodiments, the invention relates to an apparatus for incrementally dispensing from a container a therapeutic composition comprising a medicament. The apparatus comprises a measuring device installed in a container and a display device apparent to the patient on the exterior of the device which is a container comprising a vessel containing pressurized contents that contains an aerosolized therapeutic composition stored, wherein the therapeutic composition comprises a therapeutic agent and a physiologically acceptable carrier, a port integral with the vessel and through which at least a portion of the therapeutic composition can be released from the vessel, a measuring device disposed in the vessel, wherein the measuring device is capable of sensing an amount of the pressurized therapeutic composition within the vessel and arranged to output a signal representative of the amount of the therapeutic composition within the vessel, a metering valve functionally associated with the port for dispensing from the vessel a pre-determined dose of the therapeutic composition, and a dispenser functionally associated with the metering value such that at least a portion of the pressurized therapeutic composition can be dispensed from the container upon actuation of the metering value. In one such embodiment, the dispenser forms a portion of a housing that supports the container, and the housing further comprises a transfer channel to direct the pre-determined dose of the therapeutic composition to a patient. In this embodiment, the ability of the patient to monitor the amount of contents in the container upon each actuation allows the patient to be sure that the proper dose has been delivered and to know such information as how much medication remains in the container, how many times the device had been actuated to release a dose of the medication, etc.

In another such embodiment, the device further provides for data logging capability. Such capability affords the collection of whatever data the device is configured to collect and store. In this way a patient and his/her attending physician can determine, for example, whether the device is operating properly, whether the patient is complying with the particular treatment regimen, the timing and frequency of dosing, etc. For example, a chronometer may be included in the apparatus to record the time series of the actuations. The ability to monitor the amount of pressurized contents in the container upon each actuation and to record the time series of actuations allows the patient and his/her clinician to assess the degree to which a patient is following the prescribed course of chronic illness treatment and to assess the time frequency of patient administered treatment of acute symptoms. A timing function may also be used, for example, to indicate to the user when the next actuation of the device is to occur. If desired, the devices may also include telemetry capability, such that data collected, for example, on device actuation, the amount of pressurized contents used and/or remaining in the vessel, etc. can be relayed to a remote data center. Data can be transmitted by any desired route, preferably through the use of telecommunications and/or computer equipment.

In the embodiments described herein, it is envisioned that the pressurized contents may comprise an aerosol and that the aerosol may comprise solid particles suspended in a gas or liquid, or comprise liquid particles suspended in a gas or liquid.

In the embodiments described herein, it is envisioned that the measuring device may be a pressure, mass, volume, or other sensor that can quantify the ambient conditions inside the container for the purpose of reliably and directly measuring the contents inside of the container. Contents within the vessel may be sensed by a mechanical, digital or analog electric/electronic or hybrid device that is designed, programmed, or calibrated to convert the internal ambient container measurement into the amount of contents remaining in the container and then converting that result into a output signal that drives or activates a device (e.g., speaker or human readable display) on the exterior of the container or other portion of the device (e.g., a speaker, a series of LED lights, a visual display, etc.) to output a signal (e.g., a sound or series of sounds; a light or series of lights; one or more alphanumeric symbols, etc.) that can be perceived by the user. For example, when the contents of the container behave as like an ideal or real gas, in preferred embodiments a pressure sensor may be used to measure the contents of the container. When the contents of the container behave as a liquid, in preferred embodiments the measuring device may be a volume sensor. In either or any case, the amount of contents within the vessel may be sensed by a digital or analog device that is designed, programmed, or calibrated to convert the volume, pressure, or other measurement into the amount of contents (preferably correlated with the amount of active ingredient or other product) remaining in the container and then converting it into a signal output by a device in manner that allows the user to perceive, for example, the amount of contents remaining in the container. Other, less quantitative, readouts may also be used. For example, the device may simply indicate that sufficient contents remain (or do not remain) in the container for at least one more actuation and delivery of a desired dosage.

Other features and advantages of the invention will be apparent from the following drawings, detailed description, and appended claims.

BRIEF DESCRIPTION OF THE FIGURES

The following drawings form part of the present specification and are included to further demonstrate certain aspects and embodiments of the present invention. The invention may be better understood by reference to one or more of these drawings in combination with the detailed description of specific embodiments presented herein.

FIG. 4 is a functional view of a volume sensor with two embodiments of devices according to the invention.

Figure 1:
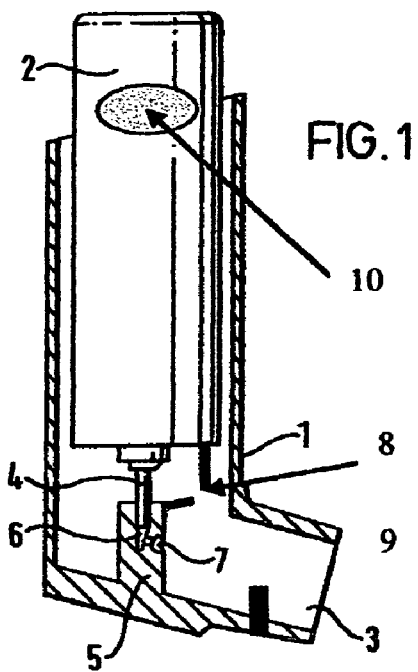
FIG. 1 is a schematic side view of a pressurized Metered Dose Inhaler, (pMDI). Several features of the device are also indicated. As will be appreciated, elements 1-6 may be found in conventional MDIs.

As those in the art will appreciate, the embodiments represented in the attached drawings are representative only and do not depict the actual scope of the invention. These and other representative embodiments are described below in greater detail.

DETAILED DESCRIPTION

As those in the art will appreciate, the following detailed description describes certain preferred embodiments of the invention in detail, and is thus only representative and does not depict the actual scope of the invention. Before describing the present invention in detail, it is understood that the invention is not limited to the particular aspects and embodiments described, as these may vary. It is also to be understood that the terminology used herein is for the purpose of describing particular embodiments only, and is not intended to limit the scope of the invention defined by the appended claims.

The present invention sets forth containers for incrementally dispensing pressurized contents. The containers comprise a vessel suited to contain pressurized contents, a port integral with the vessel and through which pressurized contents contained in the vessel can be released from the vessel, and a measuring device disposed in the vessel. The vessels are made of plastic coated glass, aluminum, steel, polyethyleneterephthalate (PET), or another other material suitable for containing contents of the sort to be housed in the particular instance, at the maximum pressure contemplated for the particular application. They are designed to be a reservoir for propellants and products to be dispensed from the container. Such products include, but are not limited to, medicines, paint, fuels, cooking aids, deodorants, and cleaning solutions, to name a few. In addition to products and propellants, other materials (e.g., surfactants, stabilizers, excipients, and other compounds in admixture with the active ingredient or product) may also be included, depending on the particular application. The measuring device is capable of sensing an amount of contents within the vessel, and it is configured to output a signal representative of the amount of the pressurized contents within the vessel, alone or through association with other components. For example, the measuring device may be associated with a microprocessor and related circuitry, power supply, and systems for converting an analog or digital data from a pressure sensor to a readout that can be interpreted by a user of the device. Such readouts include alphanumeric readouts on a display, needle readings on a gauge, sound output via a speaker, etc. As will be appreciated, the measuring device may also be used merely to indicate whether the container contains sufficient contents for at least one more discharge upon actuation.

Measuring devices contemplated for use in the context of the invention include pressure sensors and volume sensors. When pressure sensors are employed, any suitable pressure sensor may be employed and adapted for use in practicing the invention. In a preferred embodiment, the pressure sensor is constructed of a low-hysteresis material that is capable of slight flexing under applied pressure. In such embodiments, the pressure sensor is mounted inside the container so that a slight mechanical flexing of the pressure sensor, caused by a minute change in container internal pressure, creates either a variable capacitor, variable resistor, variable inductor, or induced material strain that is measurable by a gauge or other device capable of bringing a signal (which is proportional to changes in pressure inside the container) to the exterior of the container, for example. In some embodiments, the interface to the pressure sensor brings a voltage or current signal from the pressure sensor to the exterior of the container while preserving the integrity of the container as a pressure vessel. Standard principles of physics used in the present invention include, but are not limited to, The Ideal Gas Law, Raoult's Law, Henry's Law, and other physical relationships. In any event, the measuring device is capable of measuring a parameter correlated with the amount of contents in the vessel at a given time. Such parameters include pressure and volume. The measuring device can be placed at any suitable location within the vessel. In other words, the measuring device can be positioned at any location within the content-containing volume of the container (i.e., vessel), taking into account the particular size and shape of the internal, content-containing volume of the container, the type of sensor employed by the measuring device, etc.

When the contents within the container behave as a liquid, a volume sensor may be used as the measuring device, and the principles of Archimedes and Bernoulli may be used to explain the measurement of the liquid contents. As an example, a float (e.g., a ball float) may be attached to a spring located inside the container and functionally attached to an external gauge which is used to measure force. In such an embodiment, Hook's Law may be used, where $F=-kx$, where x is the spring displacement and k is the spring constant. Using a spring, as volume $V_t$ decreases, displacement $X_1 \rightarrow X_2$, and buoyant force $F_1 > F_2$. Since F is proportional to X, the displacement of the spring will be directly proportional to the volume of the liquid left in the container. The registered force may then be converted, for example, to an electrical signal which may then be processed and ultimately converted to a result that can be displayed to the user, for example, as an alphanumeric result on a monitor, by illuminating one or more LEDs, etc.

The present invention also sets forth devices for incrementally dispensing contents from a container according to the invention and measuring the amount of pressurized contents within the container following each actuation of the valve that releases some portion of the pressurized contents. The results of such measurements may be output in any suitable manner. For example, depending on the particular device and its configuration, the results may be used to report the amount of pressurized material remaining in the vessel, "count down", for example, the number of doses remaining in the vessel (or, alternatively, to "count up" to a maximum number of doses that may be delivered), the amount of material dispensed during any given actuation, whether the device contains sufficient material for at least one additional discharge of the desired amount of material, etc. If desired, the data used for such purposes may also be used, for example, to control subsequent discharge of contents. For example, as pressure drops in a vessel having a fixed internal volume following each incremental discharge of contents, the new pressure may be determined and, in order to dispense a consistent, precise amount of material upon the next use, used to control the period of time the valve remains open during the subsequent actuation.

The devices of the present invention comprise a container in functional relationship with a dispenser that can actuate a valve system at an exit port of the container. In many embodiments, a channel (typically a plastic tube, but any suitable material of any suitable shape) extends from at or near the bottom of the vessel up to the valve system. In preferred embodiments, the valve has a small, depressible headpiece, with a narrow channel running through it. The channel runs from an inlet near the bottom of the headpiece to a nozzle at the top. The size, shape, layout, and other configuration parameters of a particular valve system, including headpiece, channel, and nozzle, are left to the selection of those skilled in the art, depending on such factors as the material to be delivered, size of particles to generated, type of container and device, etc. In many of these embodiments, a spring pushes the headpiece up so the channel inlet is blocked by a tight seal. To actuate the apparatus, the headpiece is depressed, causing the inlet to slide below the seal and opening a passage from the inside of the container to the outside. The high-pressure propellant gas drives the gas- or liquid-suspended product (itself either a liquid or particles) up the plastic tube and out through the nozzle. The narrow nozzle serves to atomize the flowing liquid or particles, breaking it up into droplets or vapor. The particular size of the droplets will depend on many factors, which may vary depending on; for example, the composition to be expelled, the particle size (or size range) desired, the intended application, etc. As an additional example, a mechanical piston activated sprayer like a Windex bottle with non-pressurized contents would also work with the device.

In the context of the invention, a "propellant" is gas or liquid that, when used singly or in combination, exerts a high vapor pressure at room temperature. Preferably the propellant does not react in an appreciable manner with the product to be delivered as an aerosol from the device. In the context of MDIs, the propellant is pharmacologically inert. In the context of liquid propellants, they preferably have a boiling point of from about room temperature (25° C.) to about −25° C. Preferred liquid propellants are low boiling fluorocarbons, including 1,1,1,2-tetrafluoroethane (i.e., "propellant 134a" or "P134a") and 1,1,1,2,3,3,3-heptafluoron-n-propane (i.e., "propellant 227" or "P227").

In a device according to the invention, the high vapor pressure of the propellant forces an amount of the product (e.g., a drug formulation) out through the metering valve, which controls the amount of material dispensed. Liquid propellants very rapidly vaporize and disperse the drug particles, when the drug is formulated as a dry composition. Preferably, propellant is present in dispersion in an amount of at least 70 percent by weight of the dispersion, normally from about 85-99.99% by weight. Suitable propellants include, for example, a chlorofluorocarbon (CFC), such as trichlorofluoromethane (propellant 11), dichlorodifluoromethane (propellant 12), and 1,2-dichloro-1,1,2,2-tetrafluoroethane (propellant 114), a hydrochlorofluorocarbon, a hydrofluorocarbon (HFC), such as P134a and P227, carbon dioxide, dimethyl ether, butane, propane, or mixtures thereof. The propellants used in the present invention are preferably low boiling fluorocarbons. Preferred propellants are P134a, P227, and mixtures thereof, particularly for pharmaceutical applications.

In preferred embodiments, the devices of the invention are manually operated metered dose inhalers. MDIs provide a metered dose to the patient upon actuation of the device by the patient. FIG. 1 depicts a manually operated MDI capable of dispersing of pre-determined dosage of a therapeutic composition comprising a therapeutic agent to a patient. The conventional MDI device is made up of a container, a metering valve/dispenser, and an actuator. Containers are pressure vessels designed to be a reservoir for propellants, surfactants, and dissolved or suspended therapeutic agents which make up the pressurized contents of the container. The containers used in the context of the invention can be made from any material suitable for the particular intended application. With regard to MDIs, the containers are frequently made of aluminum or an aluminum alloy, although other metals not affected by the drug formulation, such as stainless steel, an alloy of copper, or tin plate, may be used. Containers may also be fabricated from glass, plastic, and ceramic materials. As is known in the art, strengthened aluminum or aluminum alloy containers can withstand particularly stressful coating and curing conditions, e.g., particularly high temperatures, which may be required for certain applications. Strengthened containers have a reduced tendency to malform under high temperatures, and include those comprising side walls and a base of increased thickness, as well as those having a substantially ellipsoidal base (which increases the angle between the side walls and the base of the can), rather than a more typical hemispherical base.

Metering valves are devices attached to the exit port of the container and functionally coupled to a dispenser. The metering valve is typically made using stainless steel parts and parts that are made of pharmacologically inert, propellant-resistant polymers, such as acetal, polyamide (e.g., nylon), polycarbonate, polyester, and fluorocarbon polymers (e.g., Teflon®), or a combination of these materials. Additionally, seals and "O" rings of various elastomeric materials (e.g., nitrile rubbers, polyurethane, acetyl resin, fluorocarbon polymers, etc.) are employed in and around the valve.

If desired, the container and/or other parts of the device that are or become exposed to the dispensed material can be coated with one or materials. In the context of MDIs, suitable coatings include fluorocarbon polymers made of multiples of one or more of tetrafluoroethylene (TFE), perfluorinated ethylene propylene, perfluoroalkoxyalkene (PFA), ethylene tetrafluoroethylene (ETFE), vinylidene fluoride, and chlorinated ethylene tetrafluoroethylene, with those having a relatively high ratio of fluorine to carbon being preferred. Such polymers may be blended with non-fluorinated polymers such as polyamides, polyimides, polyethersulfones, polyphenylene sulfides, and amine-formaldehyde thermosetting resins to improve adhesion of the polymer coating to the walls of the container.

In FIG. 1, the container and metering valve are referred to as the canister [1]. The metering valve is capable of preserving the pressurized contents and then releasing a pre-determined finite volume or finite mass of the pressurized contents upon actuation of the metering valve by a triggering movement of the dispenser [2]. The actuator [3] comprises a housing that supports the container and the dispenser; an adapter [4] arranged to provide a triggering movement of the dispenser sufficient to actuate the metered valve; and a transfer channel [5] to direct a predetermined dose of the pressurized contents to a patient upon actuation of the metering valve. The transfer channel is typically a "mouthpiece" or "nosepiece" that directs the aerosol to where it is required (such as the patients' nose or mouth) and partially controls the physical form of the aerosol output. To administer a pre-determined dose of pressurized contents, the patient grasps the top of the actuator and the bottom of the canister and pushes the components together providing a triggering movement of the dispenser sufficient to actuate the metered valve. This actuation causes the metering valve to operate for one dispensing cycle, delivering either a fixed volume (typically) or fixed mass of pressurized contents to the patient from the container. The actuator returns to a rest position and must be then actuated again to dispense subsequent pressurized contents.

Preferred examples of the devices of the present invention, namely a Measuring pressurized Metered Dose Inhaler (Mp-MDI), a Comparing Measuring pressurized Metered Dose Inhaler (CMpMDI), and a Recording Comparing Measuring pressurized Metered Dose Inhaler (RCMpMDI), begin with a conventional MDI but further include some or all of the following functional components, each of which can be included using any suitable physical embodiment. As relates specifically to MDI-type devices defined herein, the ability of such a device to directly measure the pressure within the container and inform the user of, for example, the amount of medication remaining in the container allows the user to be sure of a) the number of doses remaining in the container, and b) in more complex embodiments b) that the proper does (or quantity) has been delivered and c) to know the number of doses used and/or remaining in the container compared to the expected usage. In the context of MDIs, such features are extremely beneficial and serve to improve patient compliance and overall patient care.

As will be appreciated, in many embodiments the container, or vessel, of the device has a fixed volume for contents, determined by the particular configuration, dimensions, and application for the device. The invention also envisions containers in which the content volume is variable, and thus may be used, for example, to retain a desired internal pressure, or range of pressures, for the contents over time. Any suitable configuration of parts can be used to achieve this result. For example, in some of these embodiments the container may comprise a housing in which a piston or other part is disposed in moveable relation to the housing. In order to maintain pressure of the contents between actuations of the device, the moveable portion of the device (e.g., a piston) comprises one or more seals that engage the inner surface of the housing to provide a pressure-retaining seal in the product-propellant-containing portion (i.e., the content portion) of the container. Following actuation of the device, the pressure within the content volume will decrease by an amount reflective of the amount of contents discharged from the device. Pressure can be restored to a pre-set threshold by moving the piston to decrease the content volume by an appropriate amount. Piston movement can be achieved using any suitable drive mechanism operably connected to the piston or other moveable part. For example, a threaded shaft driven by an electric motor controlled by a microprocessor may be connected to a bottom portion of the piston. Upon actuation of the motor, the shaft rotates and drives the piston deeper into the housing, thereby decreasing the content volume. The length of time the motor operates, and thus how much the motor moves in relation to the housing, is controlled by the microprocessor. Any suitable algorithm for performing this function may be implemented. For example, the pressure sensor disposed in the content volume portion of the device may sample pressure at preset intervals. The resulting pressure data may then be analyzed by the microprocessor to determine if the desired pressure (or increase in pressure) has been achieved. If not, the motor continues to run and drive the piston into the housing until the desired pressure is achieved. Alternatively, after a particular cycle of product dispensing has been completed, the pressure can be determined and the necessary amount of piston movement calculated to achieve the necessary decrease in content volume in order to restore the pre-determined pressure (or reach some other pre-determined pressure within the housing). The motor is then actuated and the piston moved by the amount calculated to be necessary to achieve the desired pressure.

An alternative set of embodiments employs a bladder system to maintain a desired content pressure (or pressure range) within the container. As an example, an inflatable bladder disposed within the container may be expanded to decrease the effective volume (i.e., the content volume) within the vessel by an amount necessary to achieve a desired pressure. In such embodiments, components are included in the device to inflate the bladder by a desired amount, preferably at the direction of a microprocessor configured to maintain a certain pressure, or range of pressure, within the content volume of the container. These and other embodiments that allow for maintenance of pressure over time within the container, even after release of contents, are useful in providing repeatable, consistent delivery of contents even after multiple device actuations.

The signal output by the measuring devices of the present invention may be an electronic signal output to a device, e.g., analog comparator or digital computer, capable of interpreting the signal and converting it, for example, into discrete voltage levels which directly "energize" the display, or which are passed through a high impedance buffer to be read as inputs by a digital computer. Alternatively, the signal may be a hydraulic signal output to a hydraulic comparator capable of interpreting the signal and converting it into a display signal. The apparatus of the present invention may further comprise a high gain electronic or hydraulic amplifier that receives and boosts the value of the sensor signal as needed to provide adequate resolution for analog or digital computations by the comparator and/or digital computer.

The display may be either a set of one or more discrete visual signals, such as individually illuminated LED's, which are preferably coded to indicate the dose administered or remaining in the container; or the display is a text readout such as an Liquid Crystal Display, Electro Luminescent Panel, Plasma display, or other actively or passively illuminated display devices capable of depicting human readable ASCII text or icon symbology capable of showing, for example: a) the actual dosage remaining in the container compared to the maximum amount of medication in the new container; b) the comparison of the medication signals to medication administered; and/or c) a time series of the medication administered. As will be appreciated, other information may also be displayed, at the same time or, for example, by scrolling through a menu of options for a particular readout. The display may be activated by the comparator or the digital computer. The output for visualization may be an alphanumeric representation. In the embodiments described herein, the display may also be a site glass attached to the apparatus. While visual readouts are preferred, a device according to the invention may also be configured to output any readout, or combinations of readouts, that can be perceived by a particular user. For instance, the device may be configured to generate an audible signal indicative of the then-current state of the device and its contents, alone or in combination with a visual readout. As will be appreciated, the particular application and user will determine which components should be included for a particular application, and those ordinarily skilled in the art can readily implement any such embodiment in view of the descriptions provided in this specification. For example, if an audible output is desired in addition to a visual output, a speaker will be also included, as will software, firmware, or other control logic and other hardware needed to actuate and drive the speaker.

As will be appreciated, preferred embodiments of the invention employ circuitry for receiving and processing various signals output by various sensors and devices integrated into a container or dispensing apparatus according to the invention. Such signals include those output by a measuring device that represent the amount of contents then in the vessel portion of the container, timing signals output from a chronometer functionally integrated into the apparatus, signals output from one or more other sensors disposed on (or in) a component of the apparatus ((e.g., a sensor for detecting metering valve actuation, a sensor for detecting user identity (which can be used to ensure that only a registered user can actuate the device), etc.). A signal, output, or data that is "representative of the amount" of the product or therapeutic composition within a vessel refers to any signal, output, or data that itself represents the amount of product then in the vessel, or which is based on, derived from, or otherwise correlated with the amount of product remaining within the vessel. A "timing signal" refers to a signal, output, or data from a chronometer that can be used to indicate the occurrence of a particular event (e.g., dispensing of contents from the container, actuation of the metering valve, etc.). For example, the signal may represent date and time, elapsed time since the last event, time elapsed from a start time (i.e., a time designated "zero", for example, the first time the metering valve of the device is actuated, the time a container is functionally associated with the device (as may occur with devices in which the container is removable), etc.). Such signals can either be analog or digital signals, and the circuitry used in a particular embodiment will be adapted to receive and process the signals accordingly.

In preferred embodiments, the circuitry will include a processor, typically a microprocessor, to perform the various data and signal processing functions to be carried out by the apparatus. Any suitable processor (preferably, a microprocessor) can be employed. Indeed, the circuitry used in general in the practice of the invention will be any suitable circuitry adapted to perform the various functions described herein, as well as such other functions that may be desired in the particular context. Certain preferred embodiments employ a circuit wherein the control logic for the processor is embedded in the circuit hardware, while in other embodiments, the control logic may be provided as software stored in a memory and executed by the processor. Of course, combinations of control logic, some embedded, some software, may also be employed. To achieve maximum energy efficiency, however, most preferred are circuits that contain control logic embedded therein. Of course, in embodiments where that provide a capacity to upgrade over time some or all of the control logic, variables, or other executables necessary to perform the desired functions, appropriate circuitry can be employed.

In preferred embodiments, the circuitry will also provide a memory for storing data, and, if desired, control logic, variables, look up tables for comparing calculated results (e.g., results calculated from data obtained the measuring device) with standards (for example, data known to correspond to a particular amount of material remaining in the container, the number of uses left in the container, the number of actuations made, etc.), and/or other executables. Any suitable memory device, or combination of memory devices, can be employed. These include permanent and removable (or pluggable) memory devices. As will be appreciated, such devices can be used for a variety of purposes, including data logging. The storage capacity and configuration of a particular memory depends on many factors, and thus its implementation in a particular embodiment is left to the discretion of the skilled artisan.

As will be appreciated, the various components comprising the circuitry portion of a particular apparatus or device according to the invention will be configured such that the appropriate components are in electrical communication with each other. Further, if desired the circuitry can include one or more ports or other facilities for connection to and/or communication with another machine (i.e., the different machines, or their components, are in configured for "communicative connection"), for example, another computer or storage device adapted for receipt storage, and if desired, provision or transmission (in any suitable manner) of data to another machine adapted to receive such data. Transmission may be by any suitable method, including wireless transmission. When data is transmitted wirelessly, a receiver configured to receive the data transmitted from the apparatus is also provided, alone, as part of, or in conjunction with other equipment configured to receive, analyze, retransmit, store, and/or output results based on the data received. In preferred embodiments, an apparatus will include components that provide telemetry capability. Such components include transmitters, receivers, and/or transceivers and associated hardware (and, if necessary in the particular configuration, software).

For devices of the invention that require a source of electrical power to perform one or more functions (e.g., operation of the included measuring device, processor, memory, transmitter, etc.), the apparatus preferably includes an onboard source of electrical energy, typically in the form of one or more batteries. Batteries may be non-rechargeable, rechargeable, or replaceable, depending on the needs of the particular device. In embodiments that include one or more batteries, it may be desirable to include a facility to indicate the charge state of the battery(ies) to the user.

The apparatus of the present invention may further comprise other elements, for example, a chronometer to record the time series of the actuations, storage devices for logging data (for example, on device use, content usage, etc.), a transmitter and antennae for transmitting data to a receiving station, a port adapted for connecting the device to a computer or other machine into which data stored in the device can be downloaded and/or from which software and/or data may be uploaded, etc. The apparatus may also be configured to provide an alarm (e.g., sound, flashing light, etc.) or other output or signal that can be perceived by a user to indicate that a particular actuation of the metering valve did not result in the delivery of a desired amount of contents. Such an alarm may be particularly useful in the context of an apparatus for the delivery of a specified amount of a therapeutic composition. Whether such an alarm or other signal should be output following a particular dispensing of product can be determined using any suitable approach, including using the output of the measuring device to determine whether the desired amount of contents had, in fact, been dispensed. Other approaches include monitoring the amount of product discharged through the metering valve, the time which the metering valve remained open, the amount of material traveling though the dispensing or delivery portion of the device, etc. Depending on the particular approach to be taken, if necessary the needed sensor(s) and other components can be included in the apparatus.

Another feature that may be included in preferred embodiments is a security feature. A security feature refers to a series of components intended to ensure that only a designated user (or set of users) can actuate the apparatus to dispense contents from the container. Such components preferably provide a lock function, such that actuation of the metering valve is prevented unless a designated user enabled the actuation, for example, by entering a combination or key to unlock to the lock, by passing a component within range of a proximity reader, or by providing a fingerprint or other personal identifier required to enable dispensing function.

One class of pressurized contents contemplated for delivery using the devices of the invention is aerosols. Aerosols may comprise solid particles suspended in a gas, or they may comprise liquid particles suspended in a gas. Various techniques are known for generating aerosols, see, e.g., U.S. Pat. Nos. 6,557,552 and 5,743,251. Thus, one method for dispensing aerosol drug formulations involves making a suspension formulation of the drug as a finely divided powder in a liquefied propellant. As described herein, the suspension is stored in a sealed container that can withstand the pressure required to keep the propellant liquefied. The suspension is dispersed by activation of a dose-metering valve affixed to the container. The metering valve preferably consistently releases a fixed, predetermined amount of the drug formulation upon each activation. As the suspension is forced from the container through the dose-metering valve by the high vapor pressure of the propellant, the propellant rapidly vaporizes leaving a fast moving cloud of very fine particles of the drug formulation. The particle cloud is directed into the nose or mouth of a patient by a channeling device such as an open-ended cylinder or cone. Concurrently with activating the metering valve, the patient inhales the particles. In addition, an aerosol may comprise a first liquid (e.g., a medicine) suspended in a second liquid (e.g., a pressurized, liquefied propellant) in which the first liquid is immiscible.

In the context of therapeutic devices, the droplet or particle size of the particular drug to be delivered should allow inhalation of a sufficient portion of the drug so as to achieve the intended therapeutic benefit. For pulmonary administration, the desired droplet or particle size is preferably less than about 100 microns. Particularly preferred are droplet or particle sizes that range from about 1-10 microns, especially about 1-5 microns, in mean diameter. In practice, the final aerosol formulation desirably contains a weight to weight ratio of drug relative to the total weight of the drug formulation of about 0.005-10%, in particular 0.005-5%, especially 0.01-1.0%.

Some compounds for aerosol delivery (e.g., certain drugs) may adhere to the inner surfaces of a device according to the invention, i.e., walls of the can, valves, and caps, of an MDI, particularly with hydrofluoroalkane (i.e, "fluorocarbon") propellant systems, for example, P134a and P227, which have begun to replace chlorofluorocarbon propellants such as P11, P114, and P12. This can be of particular concern in the context of therapeutic applications. As such adherence may lead to the patient getting significantly less than the prescribed amount of drug upon each activation of the MDI. This problem can be resolved by coating the interior surfaces of the vessel and other device components (particularly those that are metallic) exposed to the drug suspension with a material (e.g., a fluorocarbon polymer, a combination of a fluorocarbon polymer and one or more non-fluorocarbon polymers, etc.) to reduce, and preferably essentially eliminate, such problems.

When utilizing the MDI-type devices of the present invention, it is recommended that actuation occur at room temperature (25° C.) and that the user thoroughly agitates the container prior to actuation.

Table 1 illustrates the embodiments that are compatible with one another:

TABLE 1

| Functional Component | MpMDI | CMpMDI | RCMpMDI | Embodiment | Digital Electronic | Analog Electronic | Mechanical Hydraulic |
|---|---|---|---|---|---|---|---|
| Pressure, Volume, Mass, Sensor in CONTAINER | Yes | Yes | Yes | 1) Variable Capacitor 2) Variable Inductor/Voice Coil 3) Strain Gage 4) Elastic Pressure Bulb 5) Load Cell | 1, 2, 3, 5 | 1, 2, 3, 5 | 4 |
| Analog Computer (Amplifier) | Yes | Yes | Yes | 1) High gain electronic amplifier 2) Hydraulic Amplifier | 1 | 1 | 2 |
| Analog to Digital Conversion | Yes | Yes | Yes | 1) Analog Comparator 2) Analog Comparator w/High Impedance Buffer | 2 | 1 | N/A |
| Comparator | Yes | Yes | Yes | 1) Analog Comparator 2) Digital Computer 3) Hydraulic Comparator | 1 | 2 | 3 |
| Display | Yes | Yes | Yes | 1) Multiple LED's or OLED's 2) Liquid Crystal, Electro Luminescent or Plasma Display with text and symbols. 3) Optical Site Glass | 1, 2 | 1, 2 | 3 |
| Chronometer | No | No | Yes | 1) Date, Time recording device | 1 | N/A | N/A |
| Medication Signal Generator a.k.a. Transfer Actuation Sensors | No | Yes | Yes | 1) Micro switch 2) Transfer Channel Pressure or Flow Sensors | 1, 2 | 1, 2 | N/A |
| Container | Yes | Yes | Yes | pMDI BOM | Yes | Yes | Yes |
| Metering Valve | Yes | Yes | Yes | pMDI BOM | Yes | Yes | Yes |
| Actuator | Yes | Yes | Yes | pMDI BOM | Yes | Yes | Yes |
| Power Supply Battery | Yes | Yes | Yes | 1) Rechargeable or Replaceable DC Battery 2) AC Powersupply 3) Piezoelectric | 1, 2, 3 | 1, 2, 3 | N/A |
| Data Port | No | No | Yes | 1) USB1, 2 2) RS232 Serial 3) IEE 1386 4) Wireless Blue Tooth etc | 1, 2, 3, 4 | 1, 2, 3, 4 | N/A |

As will be appreciated, this invention applies to any drug that can be formulated as an aerosol dispersion and which can be delivered in a therapeutically efficacious way via the nasal or pulmonary route. Here, a "drug" refers to any pharmacologically active agent that, when administered to a patient appropriately responsive thereto in the desired amount, achieves the desired therapeutic effect. Drugs contemplated for use with the devices of the invention include those that may be effectively delivered via the nasal and/or pulmonary route. A drug can be a molecule of any of a variety of classes, including small molecules, proteins, polypeptides, peptides, and nucleic acids and gene delivery vehicles. Pro-drugs, or drugs which are included within a molecule that must first be metabolized in order to become activated, are also considered "drugs" for purposes of this invention. Non-limiting examples of drugs include analgesics, anginal preparations, anti-allergics, antibiotics, anti-cholinergics, anti-infectives, anti-inflammatory preparations, antihistamines, anti-tussives, bronchodilators, diuretics, peptide and non-peptide hormones, therapeutic proteins (e.g., cytokines, lymphokines, hormones, antibodies, and enzymes), peptides, xanthines, and gene delivery vehicles, such as viral vectors (e.g., recombinant retroviruses, adeno-associated viruses, herpes viruses, etc.) and non-viral vectors (e.g., "naked" DNA vectors). Representative examples of therapeutic proteins and proteins include insulin, insulin-like growth factor I, glucagons, Avonex, alpha-1 antitrypsin, Enbrel, Factor VIII, Factor IX, human growth hormone (hGH), erythropoietin (EPO), granulocyte colony stimulating factor (G-CSF), granulocyte macrophage colony stimulating factor (GM-CSF), tissue plasminogen activator (tPA), streptokinase, epithelial growth factor (EGF), platelet-derived growth factor (PDGF), an interleukin (e.g., IL-1, IL-2, and IL-6), an interferon (e.g., alpha IFN, beta IFN, and consensus IFN), hepatitis B surface antigen, Abciximab, Antegren, Copaxone, Herceptin, Infliximab, Panorex 17-1A, Rituxan, Simulect, Synagis, and Zenapax.

A "drug formulation" or "therapeutic composition" refers to a drug (or a physiologically acceptable ester, salt or solvate thereof) optionally in combination with one or more other pharmacologically active agents and optionally containing one or more physiologically acceptable carriers and/or excipients. The term "physiologically acceptable" defines a carrier that does not abrogate the biological activity and properties of the drug with which it is formulated. A "carrier" is a chemical compound that facilitates the incorporation of a drug into cells or tissues. Any suitable carrier may be employed. An "excipient" is a compound having little or no pharmacological activity (in the quantity used) but which enhances the drug formulation or the performance of the device. Representative excipients include surfactants, preservatives, flavorings, antioxidants, anti-aggregating agents, and co-solvents. In the context of the invention, therapeutic compositions comprise aerosol sprays of finely divided droplets of liquid and/or particles. A drug may be a molecule that acts locally, for example, it is effective for the treatment of respiratory or other pulmonary disorders, as well as a molecule that may be delivered systemically through absorption into the bloodstream.

Diseases, disorders, or other conditions that can be treated using a device according to the invention include asthma, blood clots (for example, in the brain, the heart, and the peripheral vasculature), various neoplasias, chronic obstructive pulmonary disease (COPD), diabetes, emphysema, cystic fibrosis, immune system disorders or dysfunctions, including auto-immune diseases (e.g., rheumatoid arthritis, psoratic multiple sclerosis, viral infections (e.g., hepatitis B and C virus infection and HIV infection), bacterial infections (e.g., tuberculosis, sepsis, etc.), migraine headaches, and osteoporosis.

The devices and methods of the present invention are useful for treating many diseases, including a neoplasia (i.e., a new and abnormal growth of tissue that is uncontrolled and progressive) or neoplasia-related disorder, including malignant tumor growth, benign tumor growth, and metastasis. Malignant tumors, benign tumors (i.e., those characterized as a non-invasive, non-metastasized neoplasm), and metastases can occur in the nervous system, cardiovascular system, circulatory system, respiratory tract, lymphatic system, hepatic system, musculoskeletal system, digestive tract, renal system, male reproductive system, female reproductive system, urinary tract, nasal system, gastrointestinal tract, dermis, and head and neck region. Representative examples of neoplasias or neoplasia-related disorders that can be treated using a device according to the invention include acral lentiginous melanoma, actinic keratoses, acute lymphocytic leukemia, acute myeloid leukemia, adenocarcinoma, adenoid cycstic carcinoma, adenomas, adenosarcoma, adenosquamous carcinoma, anal canal cancer, anal cancer, anorectum cancer, astrocytic tumors, bartholin gland carcinoma, basal cell carcinoma, benign cysts, biliary cancer, bone cancer, bone marrow cancer, brain cancer, breast cancer, bronchial cancer, bronchial gland carcinomas, carcinoids, carcinoma, carcinosarcoma, cholangiocarcinoma, chondosarcoma, choriod plexus papilloma/carcinomal chronic lymphocytic leukemia, chronic myeloid leukemia, clear cell carcinoma, colon cancer, colorectal cancer, connective tissue cancer, cystadenoma, cysts of the female reproductive system, digestive system cancer, digestive tract polyps, duodenum cancer, endocrine system cancer, endodermal sinus tumor, endometrial hyperplasia, endometrial stromal sarcoma, endometrioid adenocarcinoma, endometriosos, endothelial cell cancer, ependymal cancer, epithelial cell cancer, esophagus cancer, Ewing's sarcoma, eye and orbit cancer, female genital cancer, fibroid tumors, focal nodular hyperplasia, gallbladder cancer, gastric antrum cancer, gastric fundus cancer, gastrinoma, germ cell tumors, glioblastoma, glucagonoma, heart cancer, hemangiblastomas, hemangioendothelioma, hemangiomas, hepatic adenoma, hepatic adenomatosis, hepatobiliary cancer, hepatocellular carcinoma, Hodgkin's disease, ileum cancer, insulinoma, intaepithelial neoplasia, interepithelial squamous cell neoplasia, intrahepatic bile duct cancer, invasive squamous cell carcinoma, jejunum cancer, joint cancer, Kaposi's sarcoma, kidney and renal pelvic cancer, large cell carcinoma, large intestine cancer, larynx cancer, leiomyosarcoma, lentigo maligna melanomas, leukemia, liver cancer, lung cancer, lymphoma, male genital cancer, malignant melanoma, malignant mesothelial tumors, medulloblastoma, medulloepithelioma, melanoma, meningeal cancer, mesothelial cancer, metastatic carcinoma, mouth cancer, mucoepidermoid carcinoma, multiple myeloma, muscle cancer, nasal tract cancer, nervous system cancer, neuroblastoma, neuroepithelial adenocarcinoma nodular melanoma, non-epithelial skin cancer, non-Hodgkin's lymphoma, oat cell carcinoma, oligodendroglial cancer, oral cavity cancer, osteosarcoma, ovarian cancer, pancreatic cancer, papillary serous adenocarcinoma, penile cancer, pharynx cancer, pituitary tumors, plasmacytoma, prostate cancer, pseudosarcoma, pulmonary blastoma, rectal cancer, renal cell carcinoma, respiratory system cancer, retinoblastoma, rhabdomyosarcoma, sarcoma, serous carcinoma, sinus cancer, skin cancer, small cell carcinoma, small intestine cancer, smooth muscle cancer, soft tissue cancer, somatostatin-secreting tumor, spine cancer, squamous carcinoma, squamous cell carcinoma, stomach cancer, striated muscle cancer, submesothelial cancer, superficial spreading melanoma, T cell leukemia, testis cancer, thyroid cancer, tongue cancer, undifferentiated carcinoma, ureter cancer, urethra cancer, urinary bladder cancer, urinary system cancer, uterine cervix cancer, uterine corpus cancer, uveal melanoma, vaginal cancer, verrucous carcinoma, vipoma, vulva cancer, well differentiated carcinoma, and Wilm's tumor.

There are large numbers of anti-neoplastic agents available in commercial use in clinical evaluation, and in pre-clinical development, which could be used in the context of the present invention for treatment of neoplasia. Various classes of anti-neoplastic agents are known, including ACE inhibitors, alkylating agents, angiogenesis inhibitors, anthracyclines/DNA intercalators, anti-cancer antibiotics or antibiotic-type agents, anti-metabolites, anti-metastatic compounds, COX-2 inhibitors, hormonal anti-cancer agents, integrin antagonists, interferons and interferon antagonists and agents, MMP inhibitors, monoclonal antibodies, nitrosoureas, NSAIDs, photodynamic agents, radio/chemo sensitizers/protectors, retinoids, taxanes, and vinca alkaloids. Compounds for vaccination against tumors are also known. Other classes also exist, and because some anti-neoplastic agents operate through multiple or unknown mechanisms, they may be classified into more than one category.

Some exemplary anti-neoplastic compounds include actinomycin D, adriamycin, bleomycin, carboplatin, carmustine, celecoxib, cisplatin, chlorambucil, cyclophosphamide, dacarbazine, deracoxib, diaziquone, docetaxel, doxorubicin, epirubicin, estramustine phosphate sodium, etoposide, etoricoxib, 5-flourouracil, halotestin, hexamethylmelamine, hydroxyurea, ifosfamide, iododeoxyuridine, iproplatin, levamisole, lomustine, medol, melphalan, meloxicam, methotrexate, misonidazole, mitomycin C, mustine hydrochloride, nitrogen mustard, paclitaxel, parecoxib, Photofrin I, prednimustine, prednisone, premarin, procarbazine, rofecoxib, selenium, streptozotocin, tamoxifen, thiotepa, valdecoxib, vinblastine, vincristine, vindesine, Other drugs that can be delivered using a device according to the invention include (−)-4-amino-3,5-dichloro-alpha-[[[6-[2-(2-pyridinyl)e-thoxy]hexyl]amino]methyl]benzenemethanol, adrenaline, adrenochrome, adrenocorticotropic hormone, adrenocortical hormones, albuterol, amiloride, aminophylline, atropine, beclomethasone dipropionate, budesonide, calcitonin, chlorotetracycline, choline theophyllinate, ciclesonide, codeine, colchicine, cortisone, cromoglycate, cephalosporins, cortisone, cromolyn sodium, cyanocobalamin, diamorphine, dihydromorphine, dihydromorphinone, diltiazem, ephedrine, epinephrine, ergotamine, fenoterol, fentanyl, fluticasone, flunisolide, formoterol, glucagons, heparin, hydrocortisone, hydroxytetracycline, insulin, an interferon, ipratropium, isoprenaline, isoetharine, isoproterenol, ketotifen, lysine theophyllinate, metaproterenol, methapyrilene, mometasone furoate, morphine, narcotine, nedocromil, neomycin, noscapine, orciprenaline, oxitropium, penicillin, pentamidine, phenylephrine, phenylpropanolamine, pirbuterol, prednisolone, procaine penicillin, procaterol, reproterol, rimiterol, salbutamol, salmeterol, scopolamine, streptomycin, sulphonamides, terbutaline, tetracycline, tipredane, triamcinolone acetonide, theophylline, trypsin, and tulobuterol.

As will be appreciated, drugs can be delivered alone or in combination, either as part of the same composition or as different compositions. Moreover, when used in combination, one or more of such compounds may be delivered via the pulmonary route, whereas the other compounds may be delivered via a different route, for example, orally (e.g., in the form of a pill, tablet, or liquid) or by injection or infusion. As will be appreciated, the particular therapeutic regimen employed (in terms of drug(s) to be administered, the number and timing of doses, route of administration, etc.) will be determined by the attending physician based on many factors, including the disease or disorder to be treated, the age and condition of the patient, etc. In some cases, drugs are administered as a vaccine, in order to immunize a patient against one or more different disease-associated antigens. Drug treatment may also be used in conjunction with, or before or after, other treatments, for example, radiation and/or surgery.

In order to affect therapy, a therapeutically effective amount of the desired drug(s) should be administered to the subject. Here, a "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-humans primates) animals being particularly preferred examples. A "therapeutically effective amount" refers to an amount of an active ingredient, particularly a drug, sufficient to effect treatment when administered to a subject in need of such treatment. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (i.e., a therapeutic regimen that employs only one chemical entity as the active ingredient). For convenience, herein the term "treatment" or "treating" means any treatment of a disease or disorder, including inhibiting, preventing, or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing". The term "protection" thus includes "prophylaxis".

While MDIs and similar devices for delivering medicines to patients represent a preferred class of embodiments, the invention has application in the context of any other device designed for the delivery of pressurized contents from a container. Other classes of such devices include spray paint cans, fuel containers (e.g., for propane, liquefied natural gas, etc.), containers for gasses, such as industrial gases (e.g., hydrogen, helium, nitrogen, oxygen, etc.), air, etc., air tanks for breathing, aerosol deodorant containers, and containers for aerosolized cleaning solutions, cooking aids, air fresheners, etc. As those in the art will appreciate, devices for these and other applications that involve the delivery of pressurized contents from containers can be readily adapted based on the descriptions provided herein, including the following examples.

EXAMPLES

The following Examples are provided to illustrate certain aspects of the present invention and to aid those of skill in the art in practicing the invention. These Examples are in no way to be considered to limit the scope of the invention in any manner.

Example 1

The Electronic Measuring Pressurized Metered Dose Inhaler (MpMDI)

A MDI as depicted in FIG. 1, callouts 1-7 only, is utilized in this Example. The container is filled to capacity with a therapeutic composition comprising a therapeutic agent (hereinafter referred to as "medication"). The canister is inserted into the actuator. The actuator works traditionally.

Figure 2:
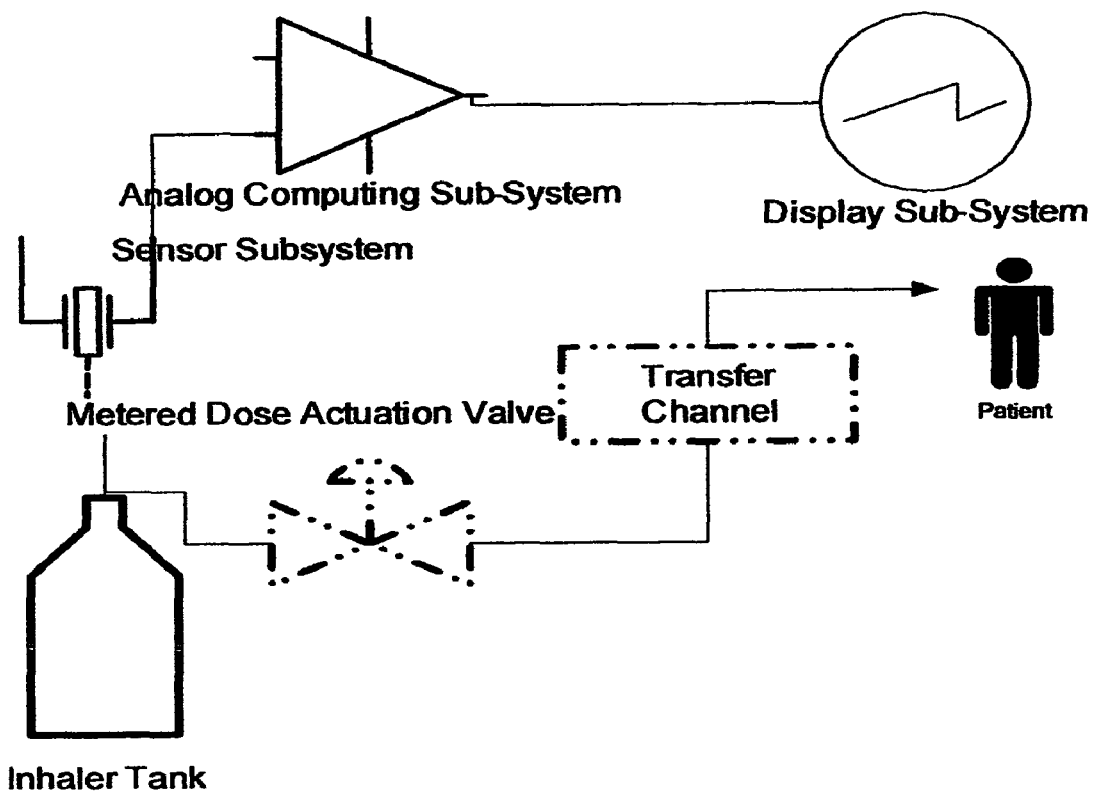
FIG. 2 is a functional view of a Measuring pMDI, (MpMDI) according to the invention.
Figure 3:
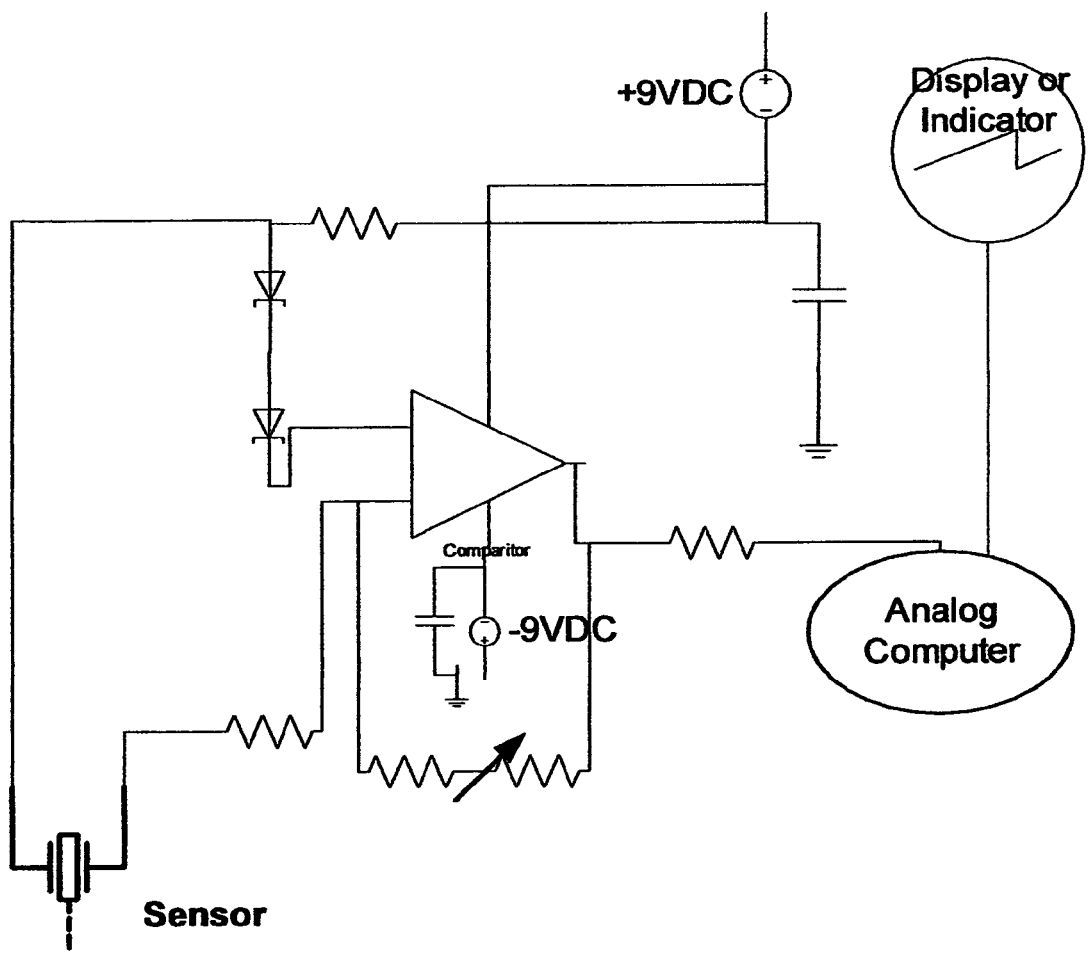
FIG. 3 is a schematic view an electric Measuring pMDI, (MpMDI) according to the invention.
Figure 5:
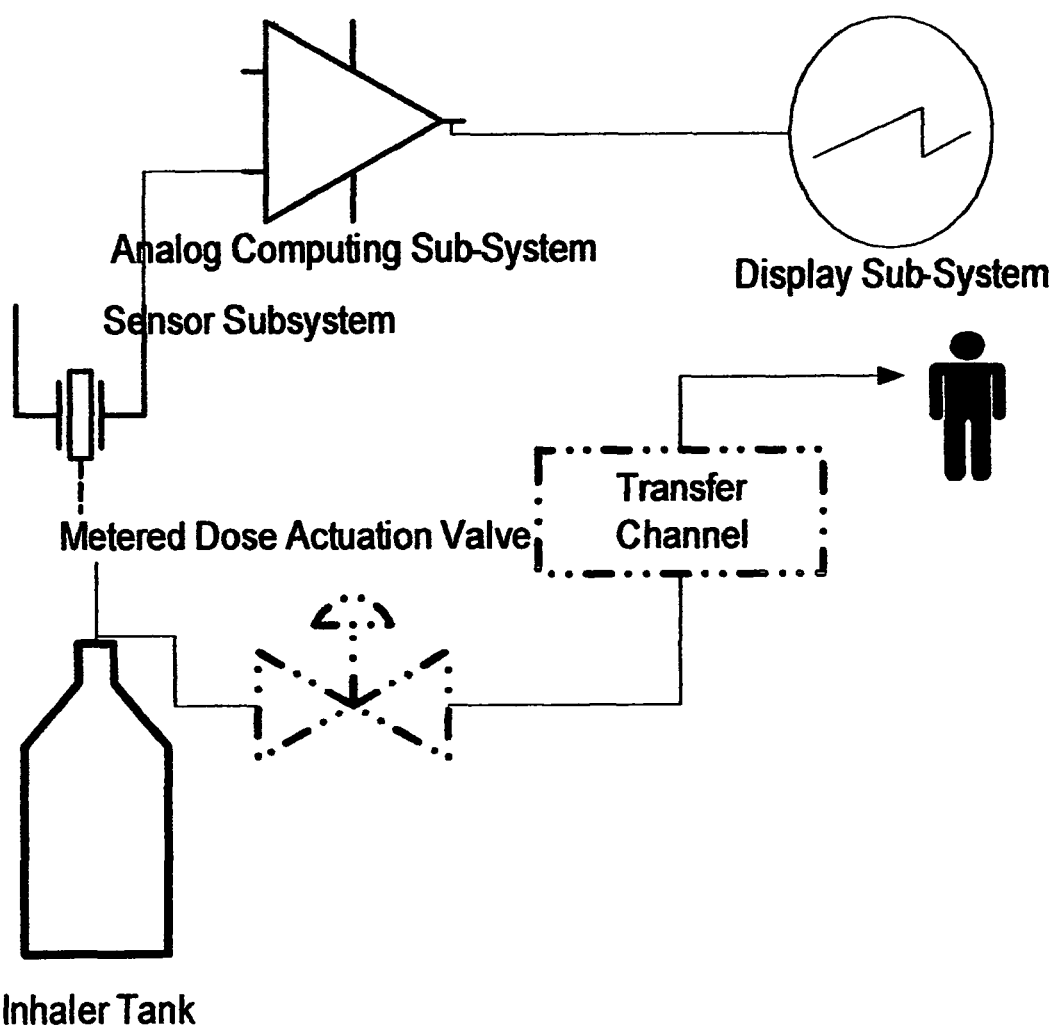
FIG. 5 is a functional view a mechanical/hydraulic Measuring pMDI, (MpMDI) according to the invention.
Figure 6:
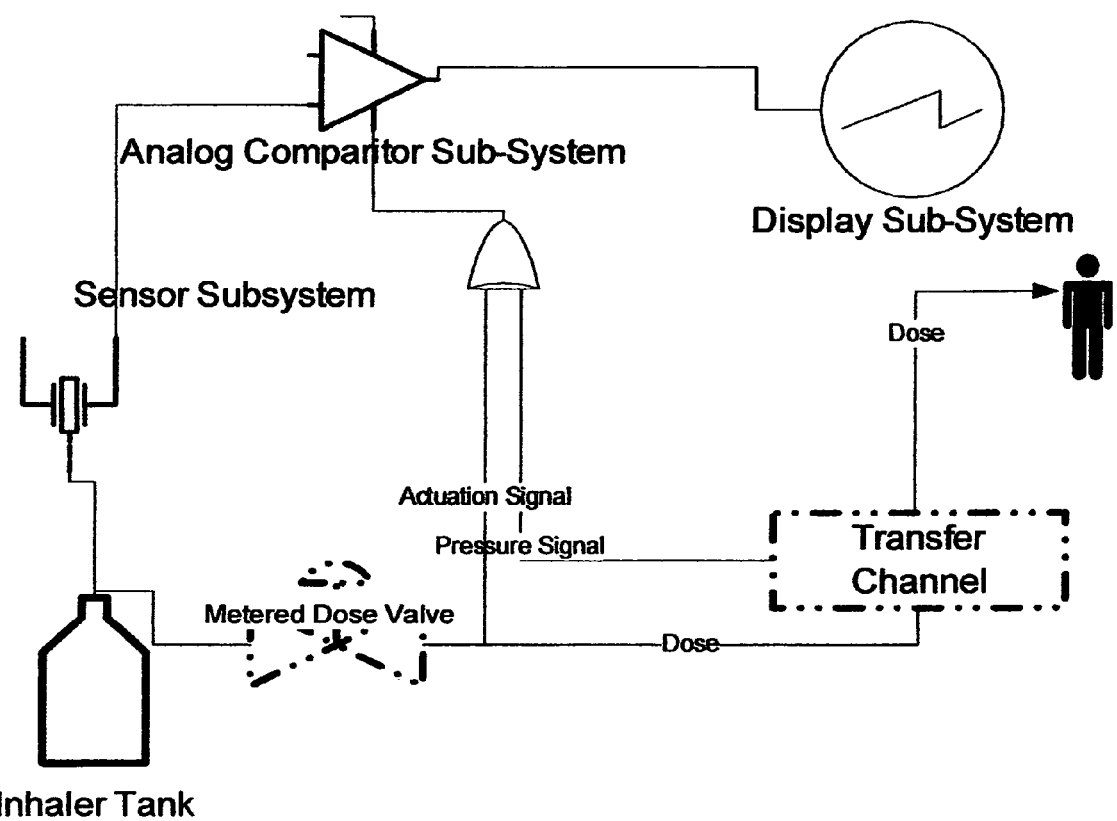
FIG. 6 is a functional view of a Comparing MpMDI (CMpMDI) according to the invention.
Figure 7:
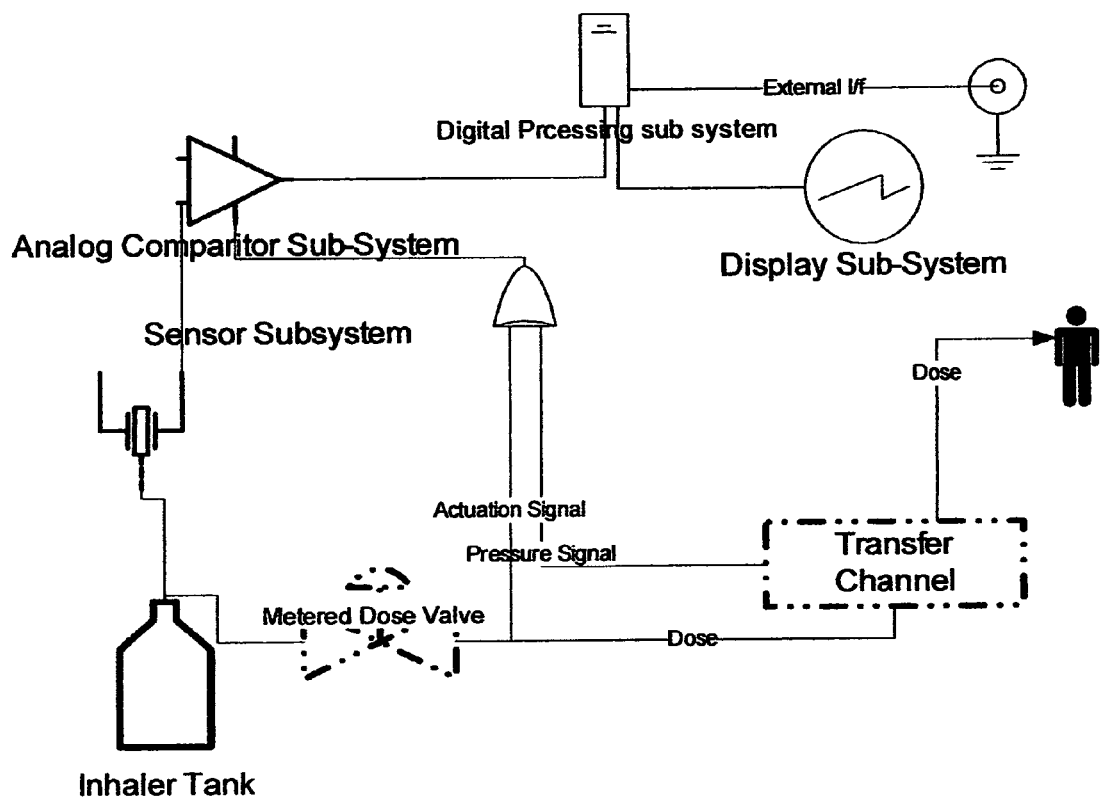
FIG. 7 is a functional view of a Recording Comparing MpMDI (RCMpMDI) according to the invention.

In this embodiment, the container includes a sensor on its interior (see FIG. 2). The sensor is either (A) a Pressure Sensor, constructed of a low-hysteresis material which is capable of slight flexing under applied pressure, and is mounted inside the container so that a slight mechanical flexing of the pressure sensor, caused by a minute change in container internal pressure, creates a variable capacitor, a variable resistor, a variable inductor or an induced material strain which is measurable by a strain gauge or other means of bringing a signal to the exterior of the container which is proportional to the change in changes in pressure inside the container; or (B) a Volume Level sensor that directly measures the contents in the container that are either of a liquid, or gas or liquid gas combination composition by using a buoyant object (Float) and Archimedes principle of buoyancy. The float is constrained and will displace a variable amount of medication as the level in the container raises or falls. This variable displacement is proportional to the buoyant force of the constrained float and directly measured by a force gage which transmits the force converted to contents outside of the container to the computing and display subsystem. An unconstrained float, i.e., allowed to move up and down with the liquid level, can move a low mass resistance wiper/actuator of a variable resistor, capacitor, or inductor and a calibration can be made to accurately determine the liquid level.

In either embodiment for this example, the device further comprises a power supply, a high gain amplifier, an analog comparator, and a display.

The actuator includes a means to interface the sensor mounted inside the container with the high gain amplifier. The interface to the sensor shall bring a voltage or current signal from the sensor to the exterior of the container while preserving the utility of the container as a pressure vessel. The amplifier boosts the value of the pressure sensor signal by approximately 20,000 times or as needed to provide adequate resolution for analog or digital computations. The comparator (which has been calibrated electronically) to model physical principles which will determine the remaining medication in the container and activate a human readable display status indication showing an accurate representation of medication remaining in the container) receives its signal from the amplifier. The amplifier signal is detected and converted by comparator circuitry into discrete voltage levels which directly "energize" the display or which are passed through a high impedance buffer to be read as inputs by a digital computer which will then activate the display.

The display is either activated by the comparator or the digital computer and is either a set of one or more discrete visual signals, such as individually illuminated LED's, which are coded to indicate the medication dose administered or remaining in the container; or the display is a text readout such as an Liquid Crystal Display, Electro Luminescent Panel, or other actively or passively illuminated display device capable of depicting, human readable ASCII text or Icon symbology showing the medication dose administered or remaining in the container.

Example 2

The Mechanical/Hydraulic Measuring Pressurized Metered Dose Inhaler (MpMDI)

A MDI as depicted in FIG. 1, callouts 1-7 only, is utilized in this Example. The container is filled to capacity with a therapeutic composition comprising a therapeutic agent (hereinafter referred to as "medication"). The canister is inserted into the actuator. The actuator works traditionally.

In this embodiment, the container includes a sensor on its interior. The sensor is either (A) a pressure sensor constructed of a low-hysteresis material which is capable of slight flexing under applied pressure, and is mounted inside the container so that a slight mechanical flexing of the pressure sensor, caused by a minute change in container internal pressure, causes a pressure reservoir, bladder or balloon to compress sending a hydraulic signal to a hydraulic amplifier; or (B) a liquid, gas or liquid gas level sensor that can consist of a buoyant object (float) that is coupled to a linkage that changes an iris or an aperture in direct proportion to the level of medication in the container.

In this embodiment, the actuator further comprises a hydraulic amplifier, a hydraulic comparator, and a display.

The device includes a means to interface the sensor mounted inside the container with the hydraulic amplifier. The interface to the sensor shall bring a hydraulic signal from the pressure to the exterior of the container while preserving the utility of the container as a pressure vessel. The comparator (which has been calibrated mechanically to model physical principles which will determine the remaining medication in the container and activate a human readable display status indication showing an accurate representation of medication remaining in the container) receives its signal from the hydraulic amplifier and the amplifier signal is converted by the comparator into a display signal. In this embodiment, the display is controlled by the comparator and is a site-glass, with one or more benchmark etchings, e.g., concentric rings, which are obscured by opaque liquid, or a site-glass iris device which shall then reveal to the patient as the amount of medication remaining in the container.

Example 3

The Electrical Comparing Measuring Pressurized Metered Dose Inhaler (CMpMDI)

A MDI as depicted in FIG. 1, callouts 1-7 and 8 or 9, or 1-9 is utilized in this Example.

In this embodiment, the actuator further comprises a medication sensor. The medication pressure sensor is a sensor in the transfer channel, or a micro switch or both. The sensor can sense the presence of medication in the transfer channel or the micro switch can sense the actuation of the metering valve, collectively or singularly called the "medication signals". Both the pressure sensor and/or micro switch closures are initiated by actuation of the metering valve.

The actuator includes a means to interface the sensor mounted inside the container and the medication sensor mounted inside the transfer channel or the actuation micro switch or both with the high gain amplifier. The amplifier boosts the value of the pressure sensor and separately the medication signal by approximately 20,000 times or as needed to provide adequate resolution for analog or digital computations. The comparator (which has been calibrated to model physical principles which will determine the remaining medication in the container and activate a human readable display status indication showing an accurate representation of medication remaining in the container) receives its signal from the amplifier, determines that a medication signal has occurred and compares theoretical vs. actual medication administered. The amplifier signal is detected and converted by comparator circuitry into discrete voltage levels which directly "energize" the display or which are passed through a high impedance buffer to be read as inputs by a digital computer which will then activate the display.

The display is either activated by the comparator or the digital computer and is either a set of one or more discrete visual signals, such as individually illuminated LED's, which are coded to indicate the medication dose administered or remaining in the container; or the display is a text readout such as an Liquid Crystal Display, Electro Luminescent Panel, or other actively or passively illuminated display device capable of depicting, human readable ASCII text or Icon symbology showing the actual dosage remaining in the container compared to the maximum amount of medication in the new container, and/or the comparison of the medication signals to medication administered.

Example 4

The Electrical Recording Comparing Measuring Pressurized Metered Dose Inhaler (RCMpMDI)

An apparatus as described in Example 3 is utilized in this Example.

In this embodiment, the comparator further comprises a digital computing subsystem, and a chronometer to record the date and time of the medicine doses administered.

The display is either activated by the comparator or the digital computer and is either a set of one or more discrete visual signals, such as individually illuminated LED's, which are coded to indicate the medication dose administered or remaining in the container; or the display is a text readout such as an Liquid Crystal Display, Electro Luminescent Panel, or other actively or passively illuminated display device capable of depicting, human readable ASCII text or Icon symbology showing: a) the actual dosage remaining in the container compared to the maximum amount of medication in the new container; b) the comparison of the medication signals to medication administered; and c) a time series of the medication administered.

All of the devices, compositions, and methods] described and claimed herein can be made and executed without undue experimentation in light of the present disclosure. While the instant devices, compositions, and methods have been described in terms of preferred embodiments, it will be apparent to those of skill in the art that variations may be applied without departing from the spirit and scope of the invention. All such variations and equivalents apparent to those skilled in the art, whether now existing or later developed, are deemed to be within the spirit and scope of the invention as defined by the appended claims. Furthermore, it is understood that the compositions, processes, machines, and articles of manufacture encompassed by the appended claims refer only to patentable embodiments. By "patentable" is meant that the particular composition(s), process(es), machine(s), and article(s) of manufacture encompassed by the particular claim includes only subject matter that satisfies all statutory requirements for patentability at the time the analysis is performed. For example, with regard to novelty, non-obviousness, or the like, if later investigation reveals that the particular claim encompasses one or more compositions, processes, machines, or articles of manufacture that would negate novelty, non-obviousness, etc., the claim, being limited by definition to "patentable" embodiments, specifically excludes the unpatentable composition(s), process(es), machine(s), or article(s) of manufacture. Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time when the validity of one or more of the appended claims is questioned, the claims are to be interpreted in a way that (1) preserves their validity and (2) provides the broadest reasonable interpretation under the circumstances.

All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A container for dispensing pressurized contents as an aerosol, comprising:
   a vessel suited to contain pressurized contents that comprise a composition that, when dispensed, is dispensed as an aerosol;
   a port integral with the vessel and through which pressurized contents contained in the vessel can be released from the vessel; and
   a measuring device disposed within the vessel, wherein the measuring device is capable of sensing an amount of the pressurized contents within the vessel and arranged to output a signal representative of the amount of the pressurized contents within the vessel.

2. A container according to claim 1 wherein the container further comprises pressurized contents that comprise a composition that, when dispensed, is dispensed as an aerosol.

3. A container according to claim 2 wherein the pressurized contents comprise a therapeutic composition and a propellant.

4. A container according to claim 3 wherein the therapeutic composition comprises a therapeutic agent and a physiologically acceptable carrier.

5. A container according to claim 4 wherein the therapeutic agent comprises is a molecule selected from the group consisting of a polypeptide and a small molecule.

6. A container according to claim 2 wherein the pressurized contents comprise a composition selected from the group consisting of a pressurized fuel, a pressurized deodorant, a pressurized cooking aid, a pressurized air freshener, a pressurized spray paint, a pressurized gas, pressurized air, and pressurized cleaning solutions.

7. A container according to claim 1 wherein the measuring device is a pressure sensor.

8. A container according to claim 1 wherein the measuring device is a mass sensor.

9. A container according to claim 1 wherein the measuring device is a volume sensor.

10. An apparatus for incrementally dispensing pressurized contents from a container, comprising:
   a container according to claim 1, wherein the container further comprises pressurized contents in the vessel; and
   a dispenser functionally coupled to the port of the container, wherein the dispenser provides for incrementally dispensing at least a portion of the pressurized contents in the vessel upon actuation of the dispenser.

11. An apparatus according to claim 10 wherein the dispenser forms a portion of a housing that supports the container.

12. An apparatus according to claim 11 wherein the housing is arranged to serve as an actuator for the dispenser.

13. An apparatus according to claim 10 wherein the signal representative of the amount of the pressurized contents within the vessel is updated after actuation of the dispenser.

14. An apparatus according to claim 13 wherein the signal is an electronic signal output to a device configured to interpret the signal and provide an output representative of the amount of the pressurized contents within the vessel.

15. An apparatus according to claim 14 wherein the device configured to interpret the signal is a microprocessor configured to convert the signal to an output used for driving a sound generator attached to the apparatus.

16. An apparatus according to claim 15 wherein the output for visualization is an alphanumeric representation of the amount of pressurized contents remaining in the container.

17. An apparatus according to claim 15 wherein the output for visualization is a schematic representation of the amount of pressurized contents remaining in the container.

18. An apparatus according to claim 15 wherein the output for visualization is a digital representation of the amount of pressurized contents remaining in the container.

19. An apparatus according to claim 15 wherein the output for visualization is an analog representation of the amount of pressurized contents remaining in the container.

20. An apparatus according to claim 15 wherein the output for visualization is an LED representation of the amount of pressurized contents remaining in the container.

21. An apparatus according to claim 15 wherein the output for visualization is an eyeglass representation of the amount of pressurized contents remaining in the container.

22. An apparatus according to claim 15 wherein the device further comprises a chronometer.

23. An apparatus according to claim 15 wherein the device comprises a memory for storing data processed by the microprocessor.

24. An apparatus according to claim 15 further comprising a transmitter for transmitting data stored in the memory to a receiver.

25. An apparatus according to claim 15 further comprising at least one port configured for communicative connection to another machine.

26. An apparatus according to claim 14 wherein the device configured to interpret the signal is a microprocessor configured to convert the signal to an output for visualization on a display attached to the apparatus.

27. An apparatus according to claim 14 wherein the device further comprises a microprocessor and a memory, wherein the microprocessor is configured to compare data stored in the memory.

28. An apparatus according to claim 10 wherein the dispenser is configured to incrementally dispense a substantially equal amount of the pressurized contents in the container upon each actuation of the actuator.

29. An apparatus for incrementally dispensing an aerosolized therapeutic composition for inhalation by a patient, comprising:
   a. a container, comprising:
      i. a vessel containing an aerosolizable composition comprising a therapeutic composition and a propellant stored under pressure, wherein the therapeutic composition comprises a therapeutic agent and a physiologically acceptable carrier;

ii. a port integral with the vessel and through which at least a portion of the aerosolizable composition can be released from the vessel; and iii. a measuring device disposed within the vessel, wherein the measuring device is capable of sensing an amount of the aerosolizable composition within the vessel and arranged to output a signal representative of the amount of the aerosolizable composition within the vessel;

b. a metering valve functionally associated with the port for dispensing a pre-determined dose of the aerosolizable composition from the vessel; and c. a dispenser functionally associated with the metering value such that at least a portion of the aerosolizable composition can be dispensed from the container upon actuation of the metering value by the dispenser.

30. An apparatus according to claim 29, wherein the dispenser forms a portion of a housing that supports the container, and wherein the housing further comprises a transfer channel to direct inhalation of the pre-determined dose of the aerosolizable composition by the patient.

31. An apparatus for incrementally dispensing an aerosolized therapeutic composition for inhalation by a patient, comprising:

a. a container, comprising:

i. a vessel containing an aerosolizable composition comprising a therapeutic composition and a propellant stored under pressure, wherein the therapeutic composition comprises a therapeutic agent and a physiologically acceptable carrier;

ii. a port integral with the vessel and through which at least a portion of the aerosolizable composition can be released from the vessel; and iii. a measuring device disposed within the vessel, wherein the measuring device is capable of sensing an amount of the aerosolizable composition within the vessel and arranged to output a signal representative of the amount of the aerosolizable composition within the vessel;

b. a metering valve functionally associated with the port for dispensing a pre-determined dose of the aerosolizable composition from the vessel;

c. a dispenser functionally associated with the metering value such that at least a portion of the aerosolizable composition can be dispensed from the container upon actuation of the metering value by the dispenser; and d. circuitry configured to receive the signal the output from the measuring device and process the signal to produce a result representative of the amount of the aerosolizable composition within the vessel.

32. An apparatus according to claim 31, wherein the circuitry includes a microprocessor in electrical communication with a memory for storing results representative of the amount of the aerosolizable composition within the vessel being stored as data.

33. An apparatus according to claim 31, wherein the circuitry includes a microprocessor in electrical communication with a memory, wherein the microprocessor is configured to compare calculated results representative of the amount of the aerosolizable composition within the vessel with data stored in the memory in order to determine how many more uses are available in the container.

34. An apparatus according to claim 31 further comprising a chronometer functionally interfaced with the circuitry, wherein the circuitry is configured to receive, process, and store in the memory a timing signal from the chronometer that corresponds to a time the metering valve is actuated to dispense a portion of the aerosolizable composition.

35. An apparatus according to claim 31, wherein the circuitry includes a capacity to transfer at least a portion of the data stored in the memory to another machine.

* * * * *